United States Patent [19]
Brodkin et al.

[11] Patent Number: 6,133,174
[45] Date of Patent: *Oct. 17, 2000

[54] MACHINABLE LEUCITE-CONTAINING PORCELAIN COMPOSITIONS AND METHODS OF MANUFACTURE

[75] Inventors: Dmitri Brodkin, West Orange; Carlino Panzera, BelleMead; Paul Panzera, Mt. Holly, all of N.J.

[73] Assignee: Jeneric/Pentron Incorporated, Wallingford, Conn.

[ * ] Notice: This patent is subject to a terminal disclaimer.

[21] Appl. No.: 09/169,410

[22] Filed: Oct. 9, 1998

Related U.S. Application Data

[60] Provisional application No. 60/062,134, Oct. 15, 1997.

[51] Int. Cl.$^7$ .......................... A61K 6/027; C03B 23/20; C03B 32/02
[52] U.S. Cl. .................. 501/6; 106/35; 501/32; 501/54; 501/66; 501/70; 501/72; 501/62; 433/201.1; 433/202.1
[58] Field of Search .................. 106/35; 501/6, 501/32, 54, 66, 70, 72, 64; 433/202.1, 201.1

[56] References Cited

U.S. PATENT DOCUMENTS

| | | | |
|---|---|---|---|
| 3,723,140 | 3/1973 | Beall et al. | 106/39.6 |
| 4,604,366 | 8/1986 | Kacicz et al. | 501/6 |
| 4,798,536 | 1/1989 | Katz | 106/35 |
| 5,204,077 | 4/1993 | Mori et al. | 423/328.2 |
| 5,527,182 | 6/1996 | Willoughby | 433/172 |
| 5,549,476 | 8/1996 | Stern | 433/223 |
| 5,698,019 | 12/1997 | Frank et al. | 106/35 |
| 5,775,912 | 7/1998 | Panzera et al. | 433/223 |
| 5,994,246 | 11/1999 | Denry | 501/32 |

FOREIGN PATENT DOCUMENTS

| | | |
|---|---|---|
| 0 543 065 | 5/1993 | European Pat. Off. . |
| 2 655 264 | 6/1991 | France . |

OTHER PUBLICATIONS

Prasad A, Vaidyanathan TK; *Crystallization of Cubic Leucite by Composition Additives+*; Prepared for Presentation at the 19$^{th}$ Annual Session, American Association for Dental Research, Mar. 9, 1990.

Denry IL, Holloway JA, Rosenstiel SF; *Crystallization Kinetics of a Low–Expansion Feldspar Glass for Dental Applications*: Journal of Biomedical Materials Research, (Sep. 5, 1998) 41 (3) 398–404.

Hahn C, Teuchert K; *Importance of the Glass Ceramic System K2O—Al2O3—SiO2 in Dental Porcelain*, Ceramic Forum International/Ber Dt. Keram Ges 57 (1980), No. 9–10, pp. 208–214.

*Primary Examiner*—C. Melissa Koslow
*Attorney, Agent, or Firm*—Ann M. Knab

[57] ABSTRACT

A method for producing a machinable feldspathic porcelain comprising leucite is presented. Machinability is imparted to feldspathic porcelains by achieving homogeneous distribution of fine crystalline constituent comprised of at least one of the following leucite phases: potassium tetragonal leucite, rubidium leucite, cesium stabilized cubic leucite, rubidium stabilized cubic leucite, and pollucite. The porcelains produced in accordance with the present invention are readily machinable by using available diamond tooling techniques. Furthermore, the porcelains are especially useful for the fabrication of dental restorations using CAD/CAM technology.

28 Claims, 1 Drawing Sheet

MACHINABLE LEUCITE-CONTAINING PORCELAIN COMPOSITIONS AND METHODS OF MANUFACTURE

CROSS REFERENCE TO RELATED APPLICATION

This application claims the benefit of U.S. Provisional Application No. 60/062,134 filed Oct. 15, 1997 which is hereby incorporated by reference, now abandoned.

BACKGROUND OF THE INVENTION

1. Field of the Invention

The present invention relates to a feldspathic porcelain for a dental restoration comprising one or more various leucite phases and the method of production thereof. More particularly, this invention relates to feldspathic porcelains which are machinable into a variety of dental articles, including dental restorations. The materials of the present invention are also especially useful for fabrication of dental restorations using CAD/CAM technology.

2. Brief Description of the Related Art

Making dental restorations is important in many situations. As human teeth grow older, they are subjected to naturally occurring breakdowns such as decay and wear. The decay of teeth is normally corrected through semi-permanent means such as fillings and the like. However, after many years, tooth decay can progress to point where restoration of the tooth through an inlay, onlay, or crown becomes necessary. Dental restorations are also important in the situation where a tooth or several teeth have been chipped, cracked and/or broken because of an accident or an act which causes a blow to the mouth. When this situation arises, the patient requires relief from the associated pain, but also desires to have the injured tooth or teeth to be restored to their appearance before the injurious event. In this situation, the dental restoration is likely to be in the form of an inlay, onlay, or crown.

Conventional methods of preparing restorations is very often time consuming for both the patient and the dentist and there is a degree of imperfection in matching the restoration to the patient's other teeth. Generally, the entire process of matching and fabricating the restoration requires more than one visit to the dentist's office. Usually, during the first visit, the dentist prepares the tooth or teeth for restoration and also fits the prepared tooth/teeth with a temporary substitute until the restoration is completed. At this first visit, an impression is taken and a working model is fabricated with individual teeth separated and indexed to be able to be precisely reassembled. Once the impression is fully prepared by the dentist, the model is then sent to a dental technician to fabricate the final dental restoration. When the dentist receives the restoration back from the technician, a fitting is performed in which the substitute restoration is removed and the final restoration is adjusted and permanently placed in the patient's mouth.

Porcelains have become the preferred material to construct a dental restoration. Porcelain dental restorations, such as crowns, bridges, and the like are highly favored because the porcelains provide strength, wear resistance, and good aesthetics. Older porcelain restorations generally comprise at least one porcelain layer on a metal framework. Newer restorations, however, generally comprise a ceramic core in place of the traditional metal, with at least one additional porcelain layer. These are commonly referred to as "all-ceramic" systems, and provide even better aesthetics than the metal-porcelain systems.

Formation of either porcelain-to-metal or all-ceramic restorations requires consideration of a number of factors, including the fusion temperature of the various layers, the size and distribution of the crystalline phase, and the materials' coefficients of thermal expansion (hereinafter CTE).

Currently available porcelain dental restorations may contain a leucite component. Leucite is a crystalline potassium aluminum silicate ($K_2O.Al_2O_3.4SiO_2$) which is used for reinforcement of feldspathic dental porcelains. At room temperature leucite ordinarily has a tetragonal configuration, and when the leucite exists in this form, it is referred to as "low leucite". The use of tetragonal leucite for reinforcement of feldspathic dental porcelains is well known and described in U.S. Pat. No. 4,604,366 to Kacicz et al., and U.S. Pat. No. 4,798,536 to Katz, all of which are incorporated by reference in their entirety.

At room temperature, leucite normally exists in the tetragonal configuration because it is the thermodynamically stable configuration of leucite at this temperature. When tetragonal leucite is heated to about 625° C. it undergoes a reversible transformation to a cubic polymorph, with a concomitant volume change of 1.2%. The cubic phase of leucite is known as "high leucite." Upon cooling to room temperature, the cubic leucite crystals revert to the more stable tetragonal polymorph.

Pollucite is a cubic compound similar to leucite and has the stoichiometric composition of $Cs_2O.Al_2O_3.4SiO_2$. U.S. Pat. No. 3,723,140 to Beall and Rittler disclose a method for forming highly crystalline glass-ceramic bodies comprising a uniform dispersion of a fine-grained pollucite phase. The approach is based on the use of self-nucleating compositions having a high alumina-to-alkali ratio, wherein the ratio of $Al_2O_3$ to the sum of $RO+R_2O$ is greater than 1.2. This ratio presumably results in the formation of submicroscopic nuclei of mullite upon which the pollucite crystals subsequently grow. However, the compositions disclosed in Beall and Rittler appear to be too refractory for use as dental restoration materials.

Other stable forms of cubic leucite have also been reported, wherein only a fraction of the potassium has been replaced by cesium, rubidium, and the like. For example, the formation of porcelains comprising cubic leucite by the volume crystallization of glasses containing about 2 mole % of $CsO_2$ has been reported by C. Hahn and K. Teuchert in "Importance of the Glass Ceramic System $K_2O$—$Al_2O_3$—$SiO_2$ in Dental Porcelain", Ceramic Forum International/Ber. Dt. Keram. Ges 57 (1980) No. 9–10, pp. 208–214, and by A. Prasad and T. K. Vaidyanathan in "Crystallization of Cubic Leucite by Composition Additives", $19^{th}$ annual session, American association of Dental Research, Mar. 9, 1990.

Feldspathic dental porcelains have superior aesthetic characteristics and have a wide use in a variety of all-ceramic restorations. Because of these qualities and others, feldspathic dental porcelains are widely used in all-ceramic dental restorations. Unfortunately, the currently available high-strength feldspathic dental porcelains are not readily machinable even when diamond tooling is the means for shaping these porcelains. Commercially available machining devices such as the Celay™ system available from Mikrona Technologie, Spreitenbach, Switzerland and the CEREC™ system manufactured by Siemens Dental Corp., Benshein, Germany, are equipped mostly with diamond tooling such as disks and/or end-mills and are sold to dental laboratories and dentists. These devices are compact in size and are quite sophisticated but have limited ability in the machining of high strength ceramics. Consequently, high strength feldspathic dental porcelains can not be used in machining devices that are employed in combination with CAD/CAM technology.

The introduction of CAD/CAM technology to the dental field has brought great enthusiasm and numerous potential applications, and is described, for example, in U.S. Pat. No. 5,549,476 to Stern, U.S. Pat. No. 5,527,182 to Willoughby, and U.S. Pat. No. 5,775,912 to Panzera et al., all of which are herein incorporated by reference in their entirety. CAD/CAM technology refers to an integrated system of computer-aided design and computer-aided manufacturing. Recently, computer reconstruction of dental restorations became commercially feasible. CAD/CAM devices are commercially availably from Siemens AG (CEREC™ system) and Elephant Holding BV (Cicero™ system); also a copy-milling system (Celay™) is available from Mikrona Technologie AG. In general, CAD/CAM systems have an optical contact digitizer which generates a computer-read signal directed to the shape of the restoration. With respect to dental restorations, commercially available CAD/CAM devices optically or mechanically read tooth areas in conjunction with dental reconstruction. This technology digitizes information from the patient's mouth or from a model of the patient's mouth using optical scanning to create a customized restoration. The use of optical impression systems, however, greatly reduces the amount of time involved in preparing a dental restoration as compared to conventional methods, but several drawbacks exist.

Generally, the accuracy of dental CAD/CAM systems is about 80–100 microns, and dental CAD/CAM devices have been used only to create inlays, onlays, and in more select instances crowns. Additionally, current machinable dental ceramics for use in CAD/CAM devices are either limited in the available shades, translucency or the ceramics require post-machining sintering/infiltration. In the dental field, at least two approaches to CAD/CAM technology are known. One approach, used in the Cerec and Celay systems, involves the use of presintered blanks and the other method used in the Procera system available from Noblepharma Inc., Goteborg, Sweden employs green bodies of ceramic material such as alumina. In the first approach, all the steps including the machining are completed in the dental office and/or the dental laboratory. The second method involves the exchange of materials and data with the central processing center where the actual machining and sintering are performed. Currently, the availability of materials for commercial CAD/CAM devices utilizing pre-sintered blanks is substantially limited to a fluormica-based glass ceramic available under the trade name Dicor MGC (commercially available from Dicor,Dentsply international, York, Pa.; porous alumina and spinel blanks available under the trade name Vita In-Ceram and sanidine-based porcelain available under the trade name Vita Mark II (both commercially available from Vita Zahnfabrick, Bad Sachingen). Machinability in Dicor MCG is associated with cleavage of mica grains. However this material has the substantial drawback that it can only be produced in limited shades. Soft sintered Vita In-Ceram alumina and spinel require the subsequent glass infiltration step following machining of the blanks and are very fragile before infiltration. The use of the Vita Mark II material suffers from the disadvantage that these blanks contain a sanidine phase which renders this material very opaque.

Despite their advantages, high-strength feldspathic porcelains have not been able to be fully utilized in the dental arts because of the associated machinability limitations. Commercially available high-strength feldspathic porcelains, such as OPC® (available from Jeneric/Pentron, Wallingford, Conn.), are currently used for hot pressing rather than machining cores for all-ceramic restorations, including crowns, inlays and onlays. These porcelains comprise 40% to 50% of a leucite phase as the reinforcement. To enhance machinability of feldspathic porcelains, the grain size of their leucite constituent should be substantially reduced and its distribution should be homogeneous throughout the glass matrix of the porcelain. However, currently, no commercial techniques are available to form in these dental porcelains the sufficient volume fraction of the leucite phase as fine-grained and uniformly dispersed as required to assure a level of machinability necessary to fabricate the complex shape of a dental restoration in an aesthetic manner.

The conventional crystallization of leucite in feldspathic glasses should be carried out at sufficiently-high temperatures, e.g. $\geq 980°$ C., to avoid crystallization of "parasitic" phases such as sanidine or feldspar. Consequently, the conventional crystallization methods may require higher crystallization temperatures to avoid formation of "parasitic" phases. However, the crystallization at these higher temperatures favors crystallization of coarser leucite particles. The presence of these coarser leucite particles inhibits the porcelains from being easily machined or used in CAD/CAM devices.

Recently, as described in pending Application No. 08/960,684 filed Oct. 30, 1997 to Denry, now U.S. Pat. No. 5,994,246, which is hereby incorporated by reference, porcelains comprising fine and uniformly dispersed cubic leucite may be manufactured by the ion-exchange of the starting glass frit with a metal salt such as rubidium nitrate. This application does not specifically teach how to use the ion-exchange method disclosed therein to produce machinable ceramics, more specifically CAD/CAM blanks.

Accordingly, there is a need for a method to produce a high-strength feldspathic dental porcelain which is readily machinable and which may be used with CAD/CAM devices.

SUMMARY OF THE INVENTION

The above-described drawbacks and deficiencies of the prior art are alleviated by the compositions and method of the present invention directed to novel high-strength feldspathic dental porcelains that are easily machinable into various dental articles by diamond tooling and the method of manufacture thereof. The porcelains of the present invention are especially useful for fabrication of dental restorations using CAD/CAM devices. Machinability is imparted to feldspathic porcelains by achieving homogeneous distribution of fine crystalline constituent comprised of at least one of the following leucite phases: potassium tetragonal leucite (low leucite), pollucite, rubidium stabilized cubic leucite (high leucite), cesium stabilized cubic leucite (high leucite), other forms of stabilized cubic leucite (high leucite) and tetragonal rubidium leucite. The porcelains produced in accordance with the present invention are readily machinable by techniques used in dental CAD/CAM devices. Furthermore, the porcelains are especially useful for the fabrication of dental restorations using CAD/CAM technology.

DETAILED DESCRIPTION OF THE INVENTION

Figure 1:
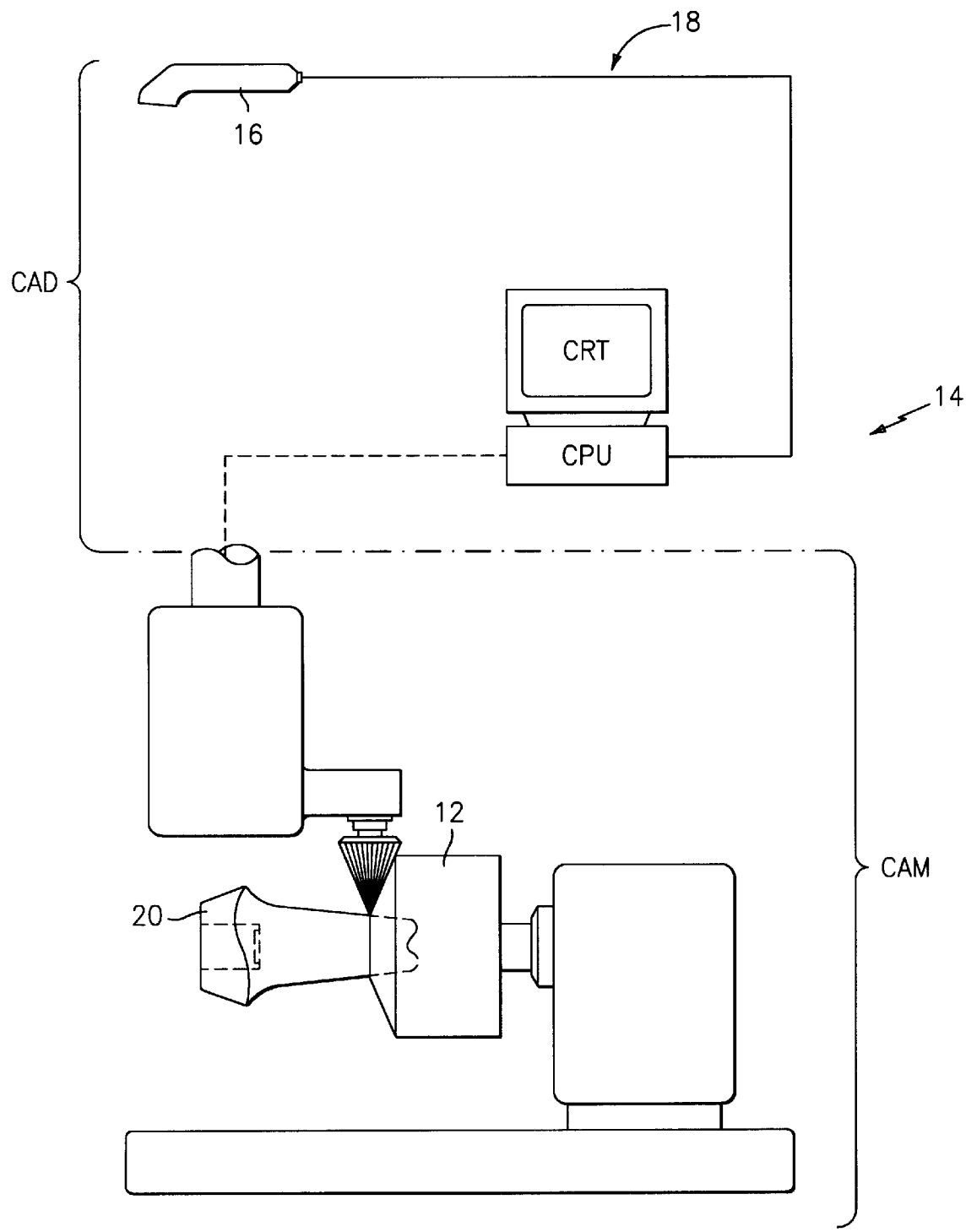
FIG. 1 is a schematic block diagram of a CAD/CAM system which may be used to design and prepare a dental restoration comprising a porcelain made in accordance with the present invention, and an illustration of a porcelain blank made in accordance with the present invention.

The present invention is directed to high-strength feldspathic porcelains that are readily machinable by available diamond tooling methods. The feldspathic porcelains of the present invention are particularly suitable for use in dental restorations and are especially useful for fabrication of dental restorations using CAD/CAM technology.

In accordance with the present invention, machinability is imparted to feldspathic porcelains by achieving homogeneous distribution of fine crystalline component comprised of one or more the following leucite phases: potassium tetragonal leucite, rubidium stabilized cubic leucite, cesium stabilized cubic leucite, other forms of stabilized cubic leucite and tetragonal rubidium leucite.

The porcelain leucite compositions of the present invention comprise a continuous glassy matrix phase and a homogenous, dispersed fine crystalline phase comprising leucite. In accordance with the method of the present invention, an amorphous glass composition is first produced from the appropriate raw materials by melting at temperatures effective to form a homogeneous glass melt. Preferably, such temperatures are in the range from about 1400° C. to about 1700° C. Preferred compositions of the amorphous glass compositions used in the present invention are shown in Table 1 below:

TABLE 1

| Oxide | Range (wt. %) | Preferred Range (wt. %) |
| --- | --- | --- |
| $SiO_2$ | 45–72 | 45–64.5 |
| $Al_2O$ | 9–19 | 12–19 |
| $B_2O_3$ | 0–16 | 0–9 |
| ZnO | 0–3 | 0–1 |
| CaO | 0–2 | 0–2 |
| MgO | 0–2 | 0–2 |
| $Li_2O$ | 0–3 | 0–3 |
| $K_2O$ | 5–16 | 11–15 |
| $Na_2O$ | 0–10 | 0–7 |
| $CeO_2$ | 0–1 | 0–0.5 |
| F | 0–2 | 0–2 |
| $Cs_2O$ | 0–9 | 0–9 |
| $Rb_2O$ | 0–7 | 0–7 |
| BaO | 0–2 | 0–2 |
| $TiO_2$ | 0–2 | 0–2 |
| $P_2O_3$ | 0–2 | 0–2 |
| $Sb_2O_3$ | 0–1 | 0–0.5 |

The amorphous glass compositions may be further modified by an ion-exchange method in which rubidium or cesium or other suitable large ion replaces the potassium in the starting glass by means of a molten salt bath as set forth in pending Application No. 08/960,684 filed Oct. 30, 1997 to Denry now U.S. Pat. No. 5,994,246 which is hereby incorporated by reference herein. The amorphous glass powder may also be produced by providing a glass that has been quenched from a melt and milling the glass into a powder by ball milling or other techniques as set forth in commonly assigned copending Application No. 60/062,345 filed on Oct. 15, 1997 now non-provisional application Ser. No. 09/168,803, filed Oct. 8, 1998, which is hereby incorporated by reference. In this method, the glass is specifically compounded to obtain the amorphous powder of the required composition with the required amount of stabilizing ion. The powder derived from this process is crystallized to yield the required leucite phase. In either instance, the ion-exchange and melting routes both serve the purpose of introducing the appropriate amount of $Rb_2O$ or $Cs_2O$ or other agent stabilizing/nucleating the required form of leucite in the amorphous glass powder. Without being bound by theory, it is believed that the presence of Rb and/or Cs in the glasses of the present invention allows the leucite phase in these glasses to crystallize at sufficiently low temperatures and still avoid crystallization of other parasitic phases, e.g. sanidine.

Surface crystallization is achieved by heat-treatment of the amorphous glass powders in one or two steps at temperatures in the range of 50–500° C. above the glass transition temperature of the amorphous glass powder for time periods in the range from about 0.5 to about 12 hours. Exact temperatures and durations are determined empirically, and depend on the composition of the glass powder, and on the desired final crystal size and distribution. For example, the temperature of the crystallization will affect nucleation density, and hence morphology of the final crystal phase as shown in copending Application No. 60/062,345 filed on Oct. 15, 1997 now non-provisional application Ser. No. 09/168,803, filed Oct. 8, 1998, which is hereby incorporated by reference.

The lower temperatures of the crystallization process in accordance with the present invention promote the fine grain size in the leucite component of the crystallized compact that is produced after the crystallization of the amorphous glass compositions. As used herein, grain size on the average is less than about five microns and preferably less than about three microns. The powder crystallization method of the present invention utilizes the tendency of the leucite phase to surface crystallization. In the absence of nucleation agents, the leucite phase has a tendency to nucleate predominantly on a surface with the nucleation front growing inward of the particle. This tendency of the leucite is commonly considered a negative attribute in the glass-ceramic field; however, in the present invention it is considered beneficial because it allows additional control of the leucite phase morphology as well as expanding the range of compositions that are suitable for use in the present invention.

As a viable alternative to the described heat-treatment, crystallization can be effected by microwave heating.

The resulting crystallized compact is pulverized into powder, which is sieved to obtain the required particle size distribution. Conventional sieving techniques may be used so that the desired particle size distribution is realized. The powder is then mixed with pigments and opacifiers to produce various color shades and translucency levels. These opacifiers and pigments are intended to be selected and used to match the color of the dental restoration with the patient's natural tooth/teeth color.

The powder is then used to form net-shaped or block-shaped pre-forms (commonly referred to as "blanks") that are particularly suitable for use in CAD/CAM devices. The blanks are dry-pressed and vacuum-sintered.

In an alternative embodiment of the present invention, a pre-crystallized glass-ceramic frit is used. The frit may be in a powder or flake form. To prepare the frit, the amorphous glass power compositions of Table 1 that have an $Al_2O_3/$(alkali oxide+alkaline earth oxide) mole ratio of about 0.75 or higher can be crystallized in bulk rather than crystallized in a powder form. In this alternative embodiment, the leucite particle size of the frit is reduced by a milling process, e.g. wet ball milling or attrition milling for extended periods of time. Either process produces a slurry of fine porcelain particles suspended in a liquid carrier such as water or alcohol. The slurry may either be directly casted, filter-pressed into blocks of the required shape or the slurry may be dried an re-fused. Casting techniques that may be employed to directly cast the slurry are the following: slip casting, filter casting, vacuum casting or centrifugal casting. If the slurry is dried and re-fused, the produced compact is processed similarly to the crystallized compact that is described herein.

In mass-production of CAD/CAM blanks other forming techniques can be utilized. For example, CIP/HIP methods may be used in which green bodies are formed in a CIP (Cold Isotactic Press) and then subsequently fired in a HIP (Hot Isotactic Press). As an alternative to the CIP procedure, the powder can be mixed with a binder and pelletized or extruded using an appropriate automatic machinery.

In the final stages of firing, diffusion homogenization occurs and the leucite phase may be partially depleted from the Rb and/or Cs. As a result, when different forms of the leucite stabilized by the presence of Rb and/or Cs are cooled, these forms can transform into tetragonal potassium leucite. This effect is used to adjust the coefficient of thermal expansion in the materials of the present invention, since different leucite species have different thermal expansion behavior. The HIP route is used in the present invention to reduce the sintering temperatures and, therefore, preserve the initial phase assemblage. The composition of the phase assemblage crystallized initially is controlled by composition of the amorphous glass powder prior to its crystallization, specifically by Rb (Cs) intake of the ion-exchanged frit or by Rb(Cs) content of the smelted flit.

The machinable feldspathic porcelains produced in accordance with the present invention have expansion in the range from about 6 to about $20 \times 10^{-6}/°$ C. (measured over 25–550° C.). The flexural strength of the present materials is more than about 120 MPa and the materials are machinable into complex shapes by diamond tooling in CAD/CAM devices. Furthermore, the porcelains can be readily pigmented and/or opacified to produce blanks of various shades and translucency levels consistent with current all-ceramic or porcelain fused to metal (PFM) dental porcelain systems. Where desired, one or more layers of the porcelain herein can be applied over the ceramic core and/or color can be baked onto the surface of the restoration to simulate tooth color.

The following examples illustrate the present invention.

EXAMPLE 1

The glass powder of the composition given below was subjected to ion-exchange in a molten bath of $RbNO_3$ for 48 hours at 500° C. Following the ion-exchange, the glass powder as rinsed 5 times, dried and heat-treated at 900° C. for 4 hours. The resulting glass-ceramic mass was then quenched into water and pulverized into powder. The glass-ceramic powder was sieved to −200 mesh and dry-pressed into 15×15×20 mm³ blocks. The blocks were sintered at 1150° C. to fall density. These blocks having a high degree of translucency were machined into various shapes required for dental restorations using a CAD/CAM device manufactured by Noble International (France).

| Oxide | wt % | mole % |
|---|---|---|
| $SiO_2$ | 68.20 | 75.15 |
| $Al_2O_3$ | 13.40 | 8.70 |
| CaO | 2.00 | 2.36 |
| $K_2O$ | 10.20 | 7.17 |
| $Na_2O$ | 6.20 | 6.62 |

EXAMPLES 2 AND 3

Examples 2 and 3 show how to prepare CAD/CAM blocks from cubic leucite-based glass-ceramics using a melt-quench method. Raw components (oxides and carbonates) were mixed by ball-milling for 1 hour to provide compositions shown in Table 2 below. The mix was charged in the coarse-grained alumina crucible and melted at 1500° C. for 4 hour. Then the temperature was rapidly increased to 1600° C., the crucible was removed from the furnace and the melt was cast into water. The resulting glass was ball-milled into a powder and sieved to −200 mesh. The glass powder was heat-treated at 980° C. for 1 hour. The glass-ceramics mass formed as a result of simultaneous crystallization and sintering of the glass powder during heat-treatment was pulverized into powder again and sieved to −200 mesh. The glass-ceramic powder was sieved to −200 mesh and dry-pressed into 15×15×20 mm³ blocks. The blocks were sintered at 1150° C. to full density.

EXAMPLE 4

This example shows how to fabricate pollucite-based glass ceramic material of low expansion. The same precursor powder that was used in Example 1 is exchanged with $CsNO_3$ instead of $RbNO_3$ as used in Example 1. All other processing steps are the same as those followed in Example 1. The resulting pollucite-based glass ceramic material exhibited a CTE of about $6 \times 10^{-6}/°$ C. (measured from 25° C. to 500° C.).

TABLE 2

| OXIDE\wt. % | Ex-2 | Ex-3 |
|---|---|---|
| $SiO_2$ | 58.6 | 59.3 |
| $B_2O_3$ | 1.0 | 1.0 |
| $Al_2O_3$ | 16.4 | 16.6 |
| $Li_2O$ | 1.1 | 1.1 |
| $K_2O$ | 12.6 | 12.7 |
| $Cs_2O$ | 7.6 | 6.5 |
| $Na_2O$ | 2.0 | 2.0 |
| F | 1.4 | 1.4 |
| 3-Pt Bend Strength, MPa | 136 ± 14 | 127 ± 17 |

The porcelains of the present invention are particularly useful for fabrication of dental restorations using CAD/CAM devices. The integrated system of computer-aided design and computer-aided manufacturing (CAD/CAM) recently gained applicability to the dental arts so that computer reconstruction of dental restorations became commercially feasible. CAD/CAM devices are commercially available from Siemens AG (CEREC system) and Elephant Holding BV (Cicero system); also a copy-milling system (Celay) is available from Mikrona Technologie AG. In general, CAD/CAM systems have an optical or contact reader which generates a computer-read signal. With respect to dental restorations, commercially available CAD/CAM devices optically or mechanically read tooth areas in conjunction with dental reconstruction. This technology digitizes information from the patient's mouth using optical scanning to create a customized restoration.

Blanks of porcelain material produced in accordance with the present invention are particularly suitable for use in CAD/CAM devices. CAD/CAM technology creates an unparalleled potential for the entire dental restoration industry because a totally customized restoration may be created by means of a CAD/CAM system. Now turning to FIG. 1, a high-strength feldspathic porcelain blank 12 of the present invention is machinable and may be milled by a CAD/CAM system. As is known in the dental arts, an impression is taken of the tooth area to be restored. An impression mold or die may be created of the tooth/teeth to be restored. The mold/die is shaped to accommodate chewing motions and to appear esthetically pleasing. The mold/die is fixed to a platform of a digitizer and then scanned with a laser, optical, or mechanical scanner designed to digitize three-dimensional surfaces to obtain an image of the final restoration.

A mechanical probe may be utilized to "feel" the surfaces and contours of the final dental restoration. Such a device is commercially available under the trade name DynaPath CNC from Autocon Corp. As the probe physically contacts the mold/die, the mechanical movements of the probe are converted into a digital image of the mold/die. After a digital image of the final dental restoration is created, the blank 12 is milled by the CAD/CAM system based upon the digitized information obtained from the scanning procedure. As shown in FIG. 1, a CAD/CAM system 14 generally consists of a digitizing scanner 16 which obtains digitized information of the mold/die. The system further contains a processing and storage means 18 that processes and stores the digitized information and properly aligns the blank for the milling process. Digitized information corresponding to the optical impression is stored for processing by the CAD program conventionally. The milling or machining of the dental restoration is carried out in conventional fashion by a computer aided machine tool based on data from the optical impression. Blank 12 is milled by the digitized information to produce a customized dental restoration 20. In accordance with the present invention, the machine tool comprises conventional diamond tooling devices.

While a CAD/CAM device has been generally described, the high-strength feldspathic porcelains of the present invention may be utilized with other CAD/CAM devices and may be machined with a conventional diamond tooling device.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. A method for the manufacture of a machinable dental porcelain composition comprising:
    providing a starting glass composition, wherein the glass composition comprises a stabilizing agent;
    crystallizing the starting glass composition to form a porcelain composition having a continuous glass matrix phase and a homogeneously dispersed crystalline phase comprising some form of leucite whereby the leucite phase has a fine grain size;
    pulverizing the porcelain composition into a powder;
    forming the powder into blocks and sintering the blocks to full density; and milling the blocks into dental restorations.

2. The method of claim 1 wherein the stabilizing agent comprises rubidium, cesium, or combinations thereof.

3. A method for the manufacture of a machinable dental porcelain composition comprising:
    providing a starting glass composition, wherein the glass composition is formed by ion-exchange of a presursor glass composition with a rubidium salt, a cesium salt, or a combination thereof;
    crystallizing the starting glass composition to form a porcelain composition having a continuous glass matrix phase and a homogeneously dispersed crystalline phase comprising some form of leucite whereby the leucite phase has a fine grain size;
    pulverizing the porcelain composition into a powder;
    forming the powder into blocks and sintering the blocks to full density; and
    milling the blocks into dental restorations.

4. A method for the manufacture of a machinable dental porcelain composition comprising:
    providing a starting glass composition, wherein the glass composition comprises about 45–72 wt % $SiO_2$, 9–19 wt % $Al_2O_3$, 5–16 wt % $K_2O$, up to 16 wt % $B_2O_3$, up to 2 wt % CaO, up to 2 wt % MgO, up to 3 wt % $Li_2O$, up to 10 wt % $Na_2O$, up to 1 wt % $Sb_2O_3$, up to 2 wt % $TiO_2$ and up to 2 wt % $P_2O_5$;
    crystallizing the starting glass composition to form a porcelain composition having a continuous glass matrix phase and a homogeneously dispersed crystalline phase comprising some form of leucite whereby the leucite phase has a fine grain size;
    pulverizing the porcelain composition into a powder;
    forming the powder into blocks and sintering the blocks to full density; and
    milling the blocks into dental restorations.

5. A method for the manufacture of a machinable dental porcelain composition comprising:
    providing a starting glass composition, wherein the glass composition comprises about 45–64.5 wt % $SiO_2$, 12–19 wt % $Al_2O_3$, 11–15 wt % $K_2O$, up to 7 wt % $B_2O_3$, up to 1 wt % ZnO, up to 2 wt % CaO, up to 2 wt % MgO, up to 3 wt % $Li_2O$, up to 7 wt % $Na_2O$, up to 0.5 wt % $CeO_2$, up to 2 wt % F, up to 0.5 wt % $Sb_2O_3$, up to 2 wt % $TiO_2$ and up to 2 wt % $P_2O_5$;
    crystallizing the starting glass composition to form a porcelain composition having a continuous glass matrix phase and a homogeneously dispersed crystalline phase comprising some form of leucite whereby the leucite phase has a fine grain size;
    pulverizing the porcelain composition into a powder;
    forming the powder into blocks and sintering the blocks to full density; and
    milling the blocks into dental restorations.

6. A method for the manufacture of a machinable dental porcelain composition comprising:
    providing a starting glass composition;
    crystallizing the starting glass composition to form a porcelain composition having a continuous lass matrix phase and a homogeneously dispersed crystalline phase comprising cubic leucite whereby the leucite phase has a fine grain size;
    pulverizing the porcelain composition into a powder;
    forming the powder into blocks and sintering the blocks to full density; and
    milling the blocks into dental restorations.

7. A method for the manufacture of a machinable dental porcelain composition comprising:

providing a starting glass composition;

crystallizing the starting glass composition to form a porcelain composition having a continuous glass matrix phase and a homogeneously dispersed crystalline phase comprising some form of leucite whereby the leucite phase has a fine grain size wherein crystallization comprises microwave heating;

pulverizing the porcelain composition into a powder; and forming the powder into machinable shapes.

8. A method for the manufacture of a porcelain leucite composition comprising:

providing a starting glass composition comprising a component that stabilizes cubic leucite at ambient temperature;

heating the starting glass composition at a temperature and for a time effective to form a glass melt;

quenching the glass melt;

grinding the quenched glass to produce a powder;

reheating the powder at a temperature and for a time effective to obtain a porcelain composition having a continuous glass matrix phase and a homogeneously dispersed, fine grain crystalline phase having a leucite phase;

pressing the powder into blocks and sintering the blocks to full density.

9. The method of claim 8 wherein the stabilizing component is rubidium, cesium, or mixtures thereof.

10. The method of claim 8 wherein the glass has a composition comprising about 45–72 wt. % $SiO_2$, 9–19 wt. % $Al_2O_3$, and 5–16 wt % $K_2O$.

11. The method of claim 10 wherein the glass composition further comprises up to 9 wt. % of one of $Cs_2O$, $Rb_2O$ or mixtures thereof.

12. The method of claim 10 wherein the glass composition further comprises up to 16 wt. % $B_2O_3$, up to 3 wt. % ZnO, up to 2 wt. % CaO, up to 2 wt. % MgO, up to 3 mole % $Li_2O$, up to 10 wt. % $Na_2O$, up to 1 wt. % $CeO_2$, up to 2 wt. % F, up to 1 wt. % $Sb_2O_3$, up to 2 wt % $TiO_2$ and up to 2 wt. % $P_2O_5$.

13. The method of claim 8 wherein the glass has a composition comprising about 45–64.5 wt. % $SiO_2$, 12–19 wt. % $Al_2O_3$, and 11–15 wt % $K_2O$.

14. The method of claim 13 wherein the glass composition further comprises up to 9 wt. % of one of $Cs_2O$, $Rb_2O$ or mixtures thereof.

15. The method of claim 13 wherein the glass composition further comprises up to 7 wt. % $B_2O_3$, up to 1 wt. % ZnO, up to 2 wt. % CaO, up to 2 wt. % MgO, up to 3 mole % $Li_2O$, up to 7 wt. % $Na_2O$, up to 0.5 wt. % $CeO_2$, up to 2 wt. % F, up to 0.5 wt. % $Sb_2O_3$, up to 2 wt % $TiO_2$ and up to 2 wt. % $P_2O_5$.

16. The method of claim 8 wherein the fine grained leucite possesses an average grain size less than about three microns.

17. The method of claim 8 wherein the porcelain leucite composition has a CTE in the range from about 12 to about $20 \times 10^{-6}/°C$. measured over the range from about 25° C. to about 500° C.

18. The method of claim 8 wherein the homogeneously dispersed, crystalline leucite phase is one of potassium tetragonal leucite, rubidium leucite, cesium stabilized cubic leucite, rubidium stabilized cubic leucite, pollucite, stabilized cubic leucite or combinations thereof.

19. The method of claim 18 wherein the homogeneously dispersed, crystalline leucite phase is cubic leucite.

20. The method of claim 8 wherein the crystallization comprises a heat treatment process carried out in one or two steps.

21. The method of claim 8 wherein the blocks are machined into dental restorations.

22. The method of claim 21 wherein the machining is performed using a computer assisted milling machine.

23. A dental restoration manufactured by the method of claim 1.

24. A dental restoration manufactured by the method of claim 4.

25. A dental restoration manufactured by the method of claim 5.

26. A dental restoration manufactured by the method of claim 6.

27. A porcelain composition manufactured by the method of claim 7.

28. A porcelain block manufactured by the method of claim 8.

* * * * *